United States Patent
Heller et al.

(10) Patent No.: US 6,638,716 B2
(45) Date of Patent: *Oct. 28, 2003

(54) RAPID AMPEROMETRIC VERIFICATION OF PCR AMPLIFICATION OF DNA

(75) Inventors: Adam Heller, Austin, TX (US); Thierry de Lumley-Woodyear, Cambridge (GB); George Georgiou, Austin, TX (US); Amihay Freeman, Ben-Shemen Youth Village (IL)

(73) Assignee: TheraSense, Inc., Alameda, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 6 days.

(21) Appl. No.: 09/145,776

(22) Filed: Aug. 24, 1998

(65) Prior Publication Data

US 2002/0001799 A1 Jan. 3, 2002

(51) Int. Cl.$^7$ .................................................. C12Q 1/68
(52) U.S. Cl. ...................... 435/6; 435/7; 435/803; 435/817; 435/810; 435/29; 435/34; 435/289.1; 935/78; 935/81; 436/501; 436/808; 436/63; 204/403; 204/415; 204/290; 204/291; 204/292
(58) Field of Search ........................... 435/6, 7, 803, 435/817, 810, 29, 34, 289.1; 935/78, 81; 436/501, 808, 63; 204/403, 415, 290, 291, 292

(56) References Cited

U.S. PATENT DOCUMENTS

| | | |
|---|---|---|
| 4,840,893 A | 6/1989 | Hill et al. |
| 4,968,602 A * | 11/1990 | Dattagupta ............... 435/6 |
| 5,147,781 A | 9/1992 | Rishpon et al. |
| 5,149,630 A | 9/1992 | Forrest et al. |
| 5,198,367 A | 3/1993 | Aizawa et al. |
| 5,262,035 A | 11/1993 | Gregg et al. |
| 5,264,104 A | 11/1993 | Gregg et al. |
| 5,320,725 A | 6/1994 | Gregg et al. |
| 5,346,832 A | 9/1994 | Aizawa et al. |
| 5,356,786 A | 10/1994 | Heller et al. |
| 5,391,272 A | 2/1995 | O'Daly et al. |
| 5,403,451 A | 4/1995 | Riviello et al. |
| 5,534,132 A | 7/1996 | Vreeke et al. |
| 5,543,132 A | 8/1996 | Baker et al. |
| 5,560,811 A | 10/1996 | Briggs et al. |
| 5,589,136 A | 12/1996 | Northrup et al. |
| 5,665,222 A | 9/1997 | Heller et al. |
| 5,906,723 A | 5/1999 | Mathies et al. |
| 5,922,183 A * | 7/1999 | Rauh ........................ 204/403 |
| 6,017,696 A | 1/2000 | Heller |
| 6,045,676 A | 4/2000 | Mathies et al. |
| 6,051,380 A | 4/2000 | Sosnowski et al. |
| 6,060,327 A | 5/2000 | Keen |
| 6,063,259 A | 5/2000 | Wang et al. |
| 6,068,818 A | 5/2000 | Ackley et al. |

FOREIGN PATENT DOCUMENTS

| | | |
|---|---|---|
| GB | 2 276 724 | 10/1994 |
| WO | WO 92/17609 | 10/1992 |
| WO | WO 97/13870 | 4/1997 |

OTHER PUBLICATIONS

Caruana, D.J. et al., "Enzyme–Amplified Amperometric Detection of Oligonucleotide Hybridization on a Microelectrode", Abstracts of Papers of the American Chemical Society, vol. 215, No. part 1, pp 282 (1998).

(List continued on next page.)

Primary Examiner—W. Gary Jones
Assistant Examiner—Janell Taylor
(74) Attorney, Agent, or Firm—Merchant & Gould P.C.

(57) ABSTRACT

Rapid electrochemical verification of the amplification of DNA by a polymerase chain reaction in a small sample of the PCR product.

24 Claims, 5 Drawing Sheets

OTHER PUBLICATIONS de Lumley–Woodyear, T. et al., "Direct Enzyme–Amplified Electrical Recognition of a 30–Base Model Oligonucleotide", J. Am. Chem. Soc., vol. 118, pp 5504–5505 (1996).

de Lumley–Woodyear, T. et al., "Rapid Amperometric Verification of PCR Amplification of DNA", Anal. Chem., vol. 71, No. 3, pp 535–538 (Feb. 1, 1999).

Uto, Y. et al., "Electrochemical Analysis of DNA Amplified by the Polymerase Chain Reaction with a Ferrocenylated Oligonucleotide", Analytical Biochemistry, vol. 250, article No. AB972207, pp 122–124 (1997).

Vreeke, M. et al., "A Thermostable Hydrogen Peroxide Sensor Based on "Wiring" of Soybean Peroxidase", Anal. Chem., vol. 67, No. 23, pp 4247–4249 (Dec. 1, 1995).

Wiedemann, D. et al., "Strategies for Low Detection Limit Measurements with Cyclic Voltammetry", Anal. Chem,, vol. 63, pp. 2965–2970 (1991).

Allongue, P. et al., "Covalent Modification of Carbon Surfaces by Aryl Radicals Generated from the Electrochemical Reduction of Diazonium Salts", J. Am. Chem. Soc, vol. 119, No. 1, pp. 201–207 (Jan. 8, 1997).

Anderson, M., "Hybridization Strategy", Gene Probes 2, A Practical Approach,Harnes and Higgins, eds., pp. 1–29 (1995).

Boni, J. et al., "Sensitive and Quantitive Detection of PCR–Amplified HTV–1 DNA Products by an Enzyme Linked Immunoassay Following Solution Hybridization with Two Differently Labeled Oligonucleotide Probes", Molecular and Cellular Probes, vol. 7, No. 5, pp. 361–371 (Oct. 1993).

Castillo, L. et al., "Analysis of Retionic Acid Receptor β Expression in Normal and Malignant Laryngeal Mucosa by a Sensitive and Routine Applicable Reverse Transcription––Polymerase Chain Reaction Enzyme–linked Immunosorbent Assay Method", Clin. Cancer Res., vol. 3, No. 11, pp. 2137–2142 (Nov. 1997).

Chu, B. et al., "Derivatization of Unprotected Polynucleotides", Nucleic Acids Res., vol. 11, No. 18, pp. 6513–6529 (1983).

de Lumley–Woodyear, T. et al., "Polyacrylamide–Based Redox Polymer for Connecting Redox Centers of Enzymes to Electrodes", Analytical Cehmistry, vol. 67, No. 8, pp. 1332–1338 (Apr. 15, 1995).

Dorenbaum, A. et al., "Transmission of HIV–1 in Infants Born to Seropositive Mothers: PCR–Amplified Proviral DNA Detected by Flow Cytometric Analysis of Immunoreactive Beads", J. Acquired Immune Defic. Syndro.&Hum. Retrovirol., vol. 15, No. 1, pp. 35–42 (May 1, 1997).

Duan, C., et al., "Separation–Free Sandwich Enzyme Immunoassays Using Microporous Gold Electrodes and Self–Assembled Monolayer/Immobilized Capture Antibodies", Anal. Chem., vol. 66, No. 9, pp. 1369–1377 (May 1, 1994).

Effenhauser, C. et al., "High –Speed Separation of Antisense Oligonucleotides on a Micromachined Capillary Electrophoresis Device", Anal. Chem, vol. 66, No. 18, pp. 2949–2953 (Sep. 151, 1994).

Green, N., "Avidin", Advances in Protein Chemistry, Anfinsen, Edsail and Richards, eds., vol. 29, pp. 85–133 (1975).

Gutiérrez, R. et al., "A Quantitive PRC–ELISA for the Rapid Enumeration of Bacteria in Refrigerated Raw Milk", J. Appl. Microbial., vol. 83, No. 4, pp. 518–523 (Oct. 1997).

Hashimoto, K. et al., "Novel DNA Sensor for Electrochemical Gene Detection", Analitica Chimica ACTA, vol. 286, No. 2, pp. 219–224 (Feb. 18, 1994).

Hashimoto, K. et al., "Sequence–Specific Gene Detection with a Gold Electrode Modified with DNA Probes and an Electrochemically Active Dye", Anal. Chem., vol. 66, No. 21, pp. 3830–3833 (Nov. 1, 1994).

Horrocks, B. et al., "Scanning Electrochemical Microscopy, 24, Enzyme Ultramicroelectrodes for the Measurement of Hydrogen Peroxide at Surfaces", Anal. Chem., vol. 65, No. 24, pp. 3605–3614 (Dec. 15, 1993).

Ivnitski, D. et al., "A One–Step, Separation–Free Amperometric Enzyme Immunosensor", Biosens. & Bioelec., vol. 11, No. 4, pp. 409–417 (1996).

Kawagoe, J. et al., "Enzyme–Modified Organic Conducting Salt Microelectrode", Anal. Chem., vol. 63, No. 24, pp. 2961–2965 (Dec. 15, 1991).

Kopp, M. et al., "Chemical Amplification: Continuous–Flow PCR on a Chip", Science, vol. 280, pp. 1046–1048 (May 15, 1998).

Korri–Youssoufi, H. et al., "Toward Bioelectronics; Specific DNA Recognition Based on an Oligonucleotide–Functionalized Polypyrrole", J. Am. Chem. Soc., vol. 119, No. 31, pp. 7388–7389 (Aug. 6, 1997).

Livache, T. et al., "Polypyrrole DNA Chip on a Silicon Device: Example of Hepatitis C Virus Genotyping", Anal. Biochem., vol. 255, No. 2, pp. 188–194 (Jan. 15, 1998).

Meyerhoff, M. et al., "Novel Nonseparation Sandwich–Type Electrochemical Enzyme Immunoassay System for Detecting Marker Proteins in Undiluted Blood", Clin Chemistry, vol. 41, No. 9, pp. 1378–1384 (1995).

Millan, K. et al., "Sequence–Selective Biosensor for DNA Based on Electroactive Hybridization Indicators", Anal. Chem., vol. 65, No. 17, pp. 2317–2323 (Sep. 1, 1993).

Millan, K. et al., "Voltammetric DNA Biosensor for Cystic Fibrosis Based on a Modified Carbon Paste Electrode", Anal. Chem., vol. 66, No. 18, pp. 2943–2948 (Sep. 15, 1994).

Napier, M. et al., "Probing Biomolecule Recognition with Electron Transfer: Electrochemical Sensors for DNA Hybridation ", Bioconjugate Chem., vol. 8, No. 6, pp. 906–913 (Nov./Dec. 1997).

Nickerson, D. et al., "Automated DNA Diagnostics Using an ELISA–Based Oligonucleotide Ligation Assay", Proc. Natl. Acad. Sci. U.S.A.., vol. 87, No. 22, p. 8923–8927 (Nov. 1990).

Ossewaarde, J. et al., "Detection of Amplified Chlamydia trachomatis DNA using a Microtiter Plate–Based Enzyme Immunoassay", Eur. J. Clin. Microbiol. Infect. Dis., vol. 13, No. 9, pp. 732–740 (Sep. 1994).

Sakai, H. et al., "Local Detection of Photoelectrochemically Produced $H_2O_2$ with a "Wired" Horseradish Perixidase Microsensor", J. Phys. Chem., vol. 99, No. 31, pp. 11896–11900 (Aug. 3, 1995).

Singhai, P. et al., "Ultrasensitive Voltammetric Detection of Underivatized Oligonucleotides and DNA", Anal. Chem., vol. 69, No. 23, pp. 4828–4832 (Dec. 1, 1997).

Takenaka, S. et al., "Electrochemically Active DNA Probes: Detection of Target DNA Sequences at Femtomole Level by High–Performance Liquid Chromatography with Electrochemical Detection", Anal. Biochem., vol. 218, No. 2, pp. 436–443 (May 1, 1994).

Vreeke, M. et al., "Direct Electrical Detection of Dissolved Bioinylated Horseradish Peroxidase, Biotin, and Avidin", Anal. Chem., vol. 67, No. 2, pp. 303–306 (Jan. 15, 1995).

Wiedemann, D. et al., "Strategies for Low Detection Limit Measurements with Cyclic Voltammetry", *Anal. Chem.*, vol. 63, p. 2965 (1991).

Xiao, L. et al., "Quantitation of RT–PCR Amplified Cytokine mRNA by Acquorin–Based Biolumminiscence Immunoassay", *J. Immunol. Methods*, vol. 199, No. 2, pp. 139–147 (1996).

Xu, X–H. et al., "Immobilization of DNA on an Aluminum(III) Alkanebisphosphonate Thin Film with Electrogenerated Chemiluminscent Detection", *J. Am. Chem. Soc.*, vol. 116, No. 18, pp. 8386–8387 (Sep. 7, 1994).

Xu, X–H. et al., "Immobilization and Hybridization of DNA on an Aluminum (III) Alkanebisphosphanate Thin Film with Electrogenerated Chemilumiscent Detection", *J. Am. Chem. Soc.*, vol. 117, No. 9, pp. 2627–2631 (Mar. 8, 1995).

* cited by examiner

RAPID AMPEROMETRIC VERIFICATION OF PCR AMPLIFICATION OF DNA

FIELD OF THE INVENTION

This invention relates in general to a method for the verification of polymerase chain reaction (PCR) amplification, and relates more specifically to a separationless electrochemical method whereby the execution of PCR is rapidly verified.

BACKGROUND OF THE INVENTION

A few hundred molecules of DNA can now be amplified by the polymerase chain reaction (PCR). Since the introduction of PCR, the time required for its execution has been considerably reduced and has now shrunk to minutes. Because a substantial fraction of the attempted PCRs do not provide the sought amplification, verification of the success of PCR is an essential process element. The practitioner of PCR must know before further using the sample prepared that the DNA was amplified as expected. Kopp, et al. (*Science* 1998, 280, 1046–7) recently carried out a rapid continuous-flow polymerase chain reaction (PCR) on a chip, amplifying a segment of the DNA of *Neisseria gonorrhoeae*. Using a micromachined chemical amplifier, they amplified, through 20 cycles, a 176-base DNA segment in periods ranging from 1.5 to 18.7 minutes. Such rapid amplification is relevant to on-site medical diagnostics and to prompt identification of environmental biological hazards, including biological warfare agents. Verification of the amplification, in a time period that is not longer than the amplification period itself, is of importance in the operation of the amplification-dependent analytical systems, because, in the absence of sufficiently rapid verification, the overall time required is limited by the duration of the verification process. Amplification of a particular DNA molecule has been usually confirmed in a two step assay, the first of which is the separation of the DNA (e.g. by gel electrophoresis) and the second of which is the detection of the separated DNA by a photonic method, based on intercalation of a light-absorbing dye or a fluorescent, chemiluminescent, or electrochemiluminescent compound and measuring the absorbed or emitted photon flux. The separations of the first step could not be carried out in minutes. One of the fastest separation methods, high speed capillary gel electrophoresis (Effenhauser, et al., *Anal. Chem* 1994, 66, 2949), still required a complex and time-consuming setup procedure.

A more rapid and simpler method for verifying amplification of DNA by PCR is needed. It is the objective of this invention to provide such a method.

SUMMARY OF THE INVENTION

The present invention provides a separationless electrochemical method whereby PCR amplification is verified. The method utilizes an electrode coated with a redox polymer film. The redox polymer film is preferably a redox hydrogel. A binding agent is immobilized in the redox polymer film, preferably through covalent bonding of the binding agent to the redox polymer. The DNA is labeled, while amplified, with two or more different ligands, the first of which binds strongly to the binding agent immobilized in the redox polymer film. When the sample in which the amplification is to be confirmed is contacted with the electrode, amplified DNA is immobilized on the electrode through linkage of the immobilized binding agent in the redox polymer film with the first ligand. The presence of the amplified DNA on the electrode is detected through exposure of the electrode to a detection marker. The detection marker is a molecule with two functional groups. One of the functional groups binds with the second ligand of the amplified DNA; the second functional groups of the detection marker produces an electrochemically detectable signal. The second functional group of the detection marker is generally a catalyst, usually an enzyme. In the preferred embodiment the catalyst of the detection marker is an oxidoreductase. When the second ligand of the immobilized amplified DNA in or on the redox polymer film binds the detection marker, the catalyst of the detection marker comes into contact with the redox polymer and becomes an electrocatalyst. As a result, when the electrode is poised at an appropriate potential, a detection compound, which in the preferred embodiment, is a substrate for the oxidoreductase, is catalytically electroreduced or electrooxidized. The electrooxidation or the electroreduction results in an increase in the current passing through the electrode. The electrode is preferably poised at a potential where little or no current flows in absence of either the redox polymer or the detection marker in or on the film on the electrode. The detection compound may be added to the solution to be tested for the amplified DNA from the PCR, or it can be internally generated in the film, by reacting stable and preferably non-toxic reactants in catalytic centers incorporated in the film. The preferred detection compound generating catalytic centers in the film are enzymes, the presence of which does not substantially increase or decrease the current resulting from the electrooxidation or electroreduction of the detection compound.

In an example of such a method, a biotin labeled primer of one nucleotide sequence and a digoxigenin labeled primer of a complementary sequence are added to the DNA amplification solution. A redox polymer film, comprising avidin, is immobilized by crosslinking on a carbon electrode. Being biotin labeled, the amplified DNA binds to the avidin on the electrode. The presence of the amplified DNA is detected by exposing the electrode to a solution of horseradish peroxidase (HRP) labeled antidigoxin. Binding of the horseradish peroxidase labeled antidigoxin to the digoxigenin function of the amplified DNA converts the film on the electrode to a catalyst for the electroreduction of hydrogen peroxide to water at a potential between about −0.1V and +0.4V versus the saturated calomel electrode (SCE) and causes the flow of an electrical current when the electrode is poised at a potential in this range. The magnitude of the current is then related to the concentration or the amount of amplified DNA.

DETAILED DESCRIPTION OF THE PREFERRED EMBODIMENT

Definitions

As used herein, the following terms and phrases have the definitions indicated:

Redox Hydrogel: A water containing, crosslinked redox polymer. The weight of water exceeds 10 wt % of the dry, crosslinked polymer.

Binding Agent: A macromolecular agent strongly and specifically binding a ligand. Examples of binding agents include avidin; streptavidin; single-stranded DNA; single-stranded oligonucleotides; single-stranded peptide DNA; antibodies and macromolecular antigens.

Ligand(s): A low molecular weight member of a specifically-binding affinity pair. Examples include biotin, digoxin and digoxigenin. Typically the molecular weight of the ligands of this invention is of less than $10^3$ daltons. Two or more chemically different ligands are covalently bound to the DNA. When two ligands are bound these are termed the first ligand and the second ligand. The second ligand binds the detection marker.

Detection Marker: A macromolecule having two functions, one specifically binding to the second ligand attached to the DNA, the other a catalyst, usually an enzyme. The preferred enzymes are oxidoreductases.

Detection Compound: A compound, the conversion or generation of which is accelerated by the catalyst of the detection marker. The preferred detection compounds are electroreduced or electrooxidized on electrodes coated with films comprising both a redox polymer and a detection marker.

Antidigoxin: An antibody or a fragment of an antibody selectively binding compounds like digoxin or digoxigenin.

Figure 1A:
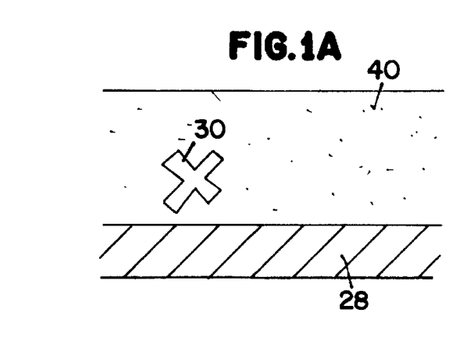
FIGS. 1A–1C are schematic drawings showing components utilized in the verification of amplification of DNA, their positions and their linkages.
Figure 1B:
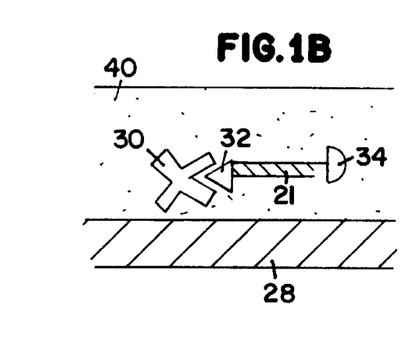
Figure 1C:
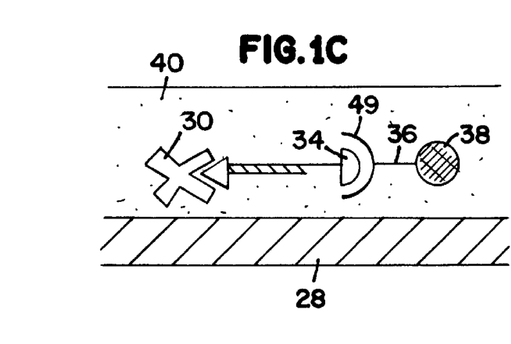
Figure 2A:
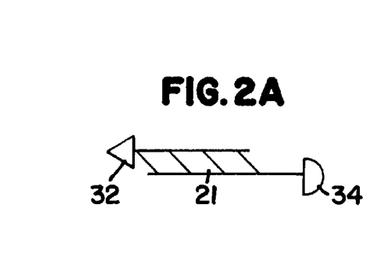
FIGS. 2A–2F are schematic drawings showing various embodiments for labeling amplified nucleic acids.
Figure 2B:
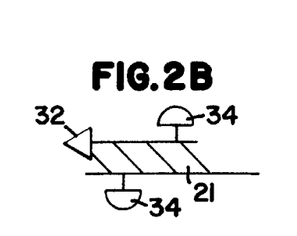
Figure 2C:
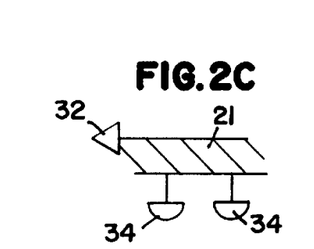
Figure 2D:
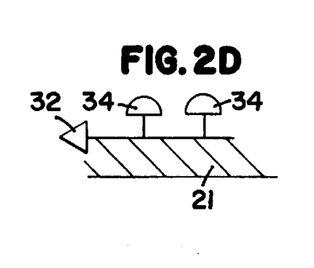
Figure 2E:
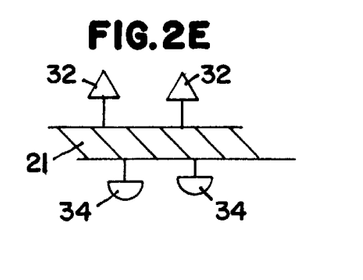
Figure 2F:
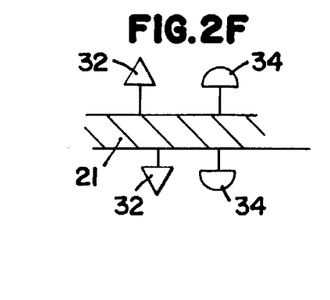

As shown in FIGS. 1A–1C, the assay system of the invention includes an electrode 28 which is coated with a redox polymer 40 in which a binding agent 30 for a first ligand 32 is immobilized (FIG. 1A). Upon PCR amplification, two chemically different ligands 32, 34 are incorporated in the amplified DNA 21 (FIG. 1B). One of these is the first ligand 32 the other is the second ligand 34. The ligands 32 and 34 may be optionally at or near the opposite termini of the amplified DNA 21 (FIG. 2A). This is the case when the ligands originate in the respective primers. Alternatively, multiple copies of the first ligand 32 or of the second ligand 34 may be incorporated along the chains forming the amplified DNA 21 (FIGS. 2B–2F). This may be accomplished by labeling one of the polymerizing components with the first ligand 32 incorporated in the chain, while incorporating the second ligand 34 in the amplified DNA 21 through the ligand-labeled primer (FIGS. 2B–2D). Alternatively, both the first 32 and second 34 ligands may be incorporated in the amplified DNA 21 by adding two different polymerizing components, one labeled with the first ligand 32, the second labeled with the second ligand 34, in which case both the first ligand 32 and second ligand 34 are distributed along the amplified DNA chain 21 (FIGS. 2E–2F). In any of these cases, illustrated in FIGS. 2A–2F, the amplified DNA 21 is labeled with both ligands 32 and 34.

Of these three labeling scenarios, the first, incorporation of the two ligands 32, 34 in the two primers and their location at opposite termini of the amplified DNA (FIG. 2A), is preferred, because using terminal ligands, both the execution of the amplification is verified and it is also verified that not only a segment of the DNA but the entire DNA was amplified.

Upon contacting of the solution containing the tested PCR product solution with the electrode 28 coated with the binding agent 30 and the redox polymer 40 comprising film, amplified DNA 21 is captured on or in the redox film through the affinity reaction between the binding agent 30 and the first ligand 32. To detect the presence of the captured amplified DNA 21 on the electrode, the captured DNA 21 is conjugated, through its second ligand 34, with the detection marker 36 (FIG. 1C).

Figure 3A:
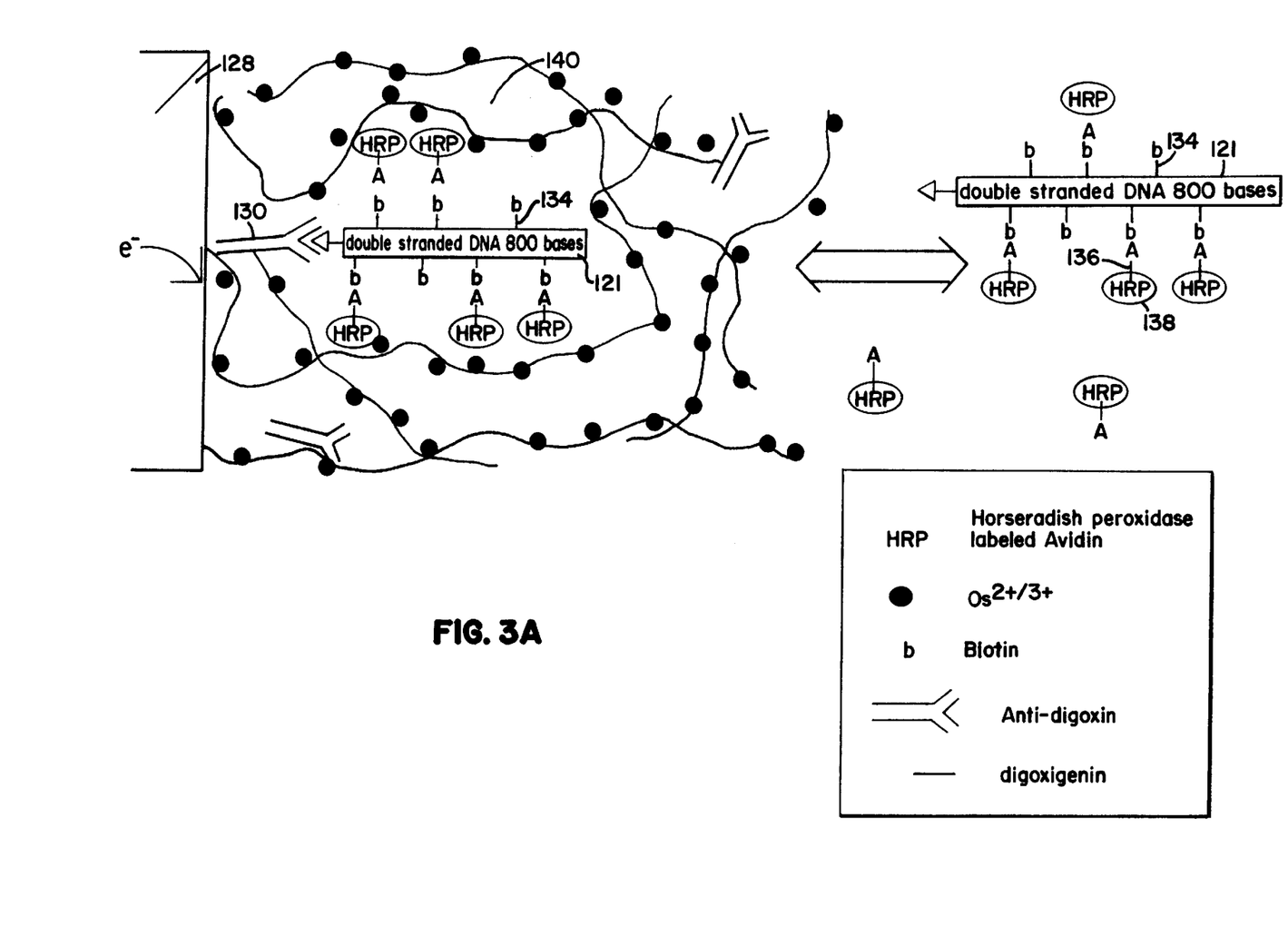
FIGS. 3A–3B are schematic drawings of an example of the verification of DNA amplification of the invention, showing the electron transfer in FIG. 3B.
Figure 3B:
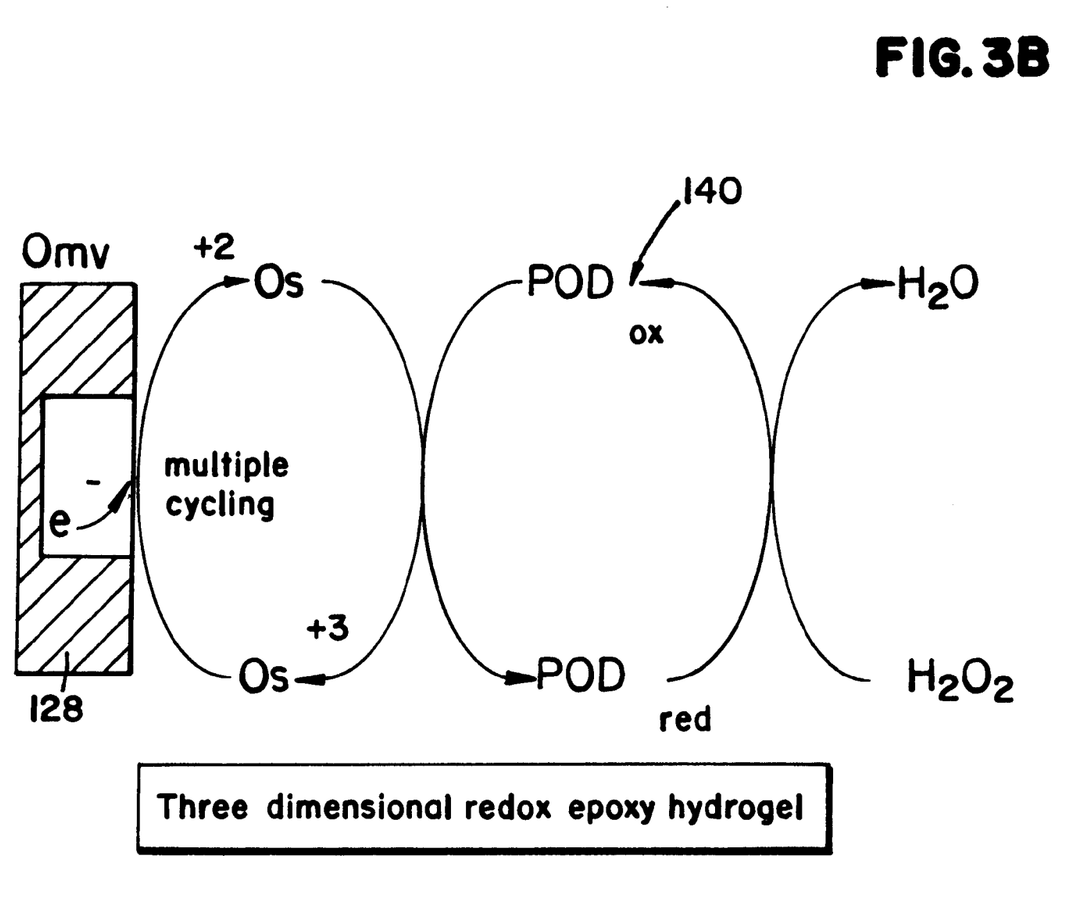

In the specific embodiment shown schematically in FIG. 3A, the PCR amplified double stranded DNA 121 reacts with and binds through its digoxigenin functions 132, to the antidigoxin 130 in the electron-conducting redox hydrogel film 140. When the biotin functions 134 of the now immobilized amplified DNA combine with avidin 136 labeled horseradish peroxidase 138, the simultaneous presence of the redox polymer 140 and the horseradish peroxidase 138 in or on the film on the electrode 128 makes the film an electrocatalyst for $H_2O_2$ electroreduction to water. The cycles involved in the electrocatalysis are shown in FIG. 3B. The current flowing during the $H_2O_2$ electroreduction reaction is correlated with the DNA amplification. As described in another copending U.S. patent application by Applicants Yarnitzky and Heller, titled "Potentiometric Sensors for Analyte Detection", U.S. Ser. No. 09/158,973, filed on the same date as the instant application and incorporated herein by reference, the verification can be carried out also by measuring a potential. As described in another copending U.S. patent application by Applicants Heller and Campbell, titled "Electrochemical Affinity Assay", Attorney Docket No. 12008.22US01, filed on the same date as the instant application and incorporated herein by reference, the hydrogen peroxide can be generated in the redox polymer film from stable and non-toxic reactants like choline and oxygen, when, for example, non-electroactive choline oxidase is immobilized in the redox polymer film.

In another embodiment of the invention, an oxidase, such as glucose oxidase, is used as catalyst 38. In this case the detection compound is glucose. Glucose is added to the tested solution and is electrooxidized on the redox polymer PAH coated electrode in or on which the detection marker with glucose oxidase is immobilized. Glucose electrooxidation takes place at potentials positive of about +0.1V versus SCE. The reaction is believed to proceed by the electrode oxidizing the redox polymer, the redox polymer oxidizing glucose oxidase, and glucose oxidase oxidizing glucose (the detection compound 50). The preferred potential at which this electrode is poised is between +0.2V(SCE) and +0.4V (SCE).

In yet another embodiment of the invention a hydrolase, such as alkaline phosphatase is used as catalyst 38. Alkaline phosphatase hydrolyzes a difficult to electrooxidize detection compound-precursor, a phosphate ester of p-aminophenol, to p-aminophenol, which is readily electrooxidized on the electrode.

The Working Electrode

The working electrode 28 is typically a solid metal or a wire or a thin film of conductive material disposed on an insulating substrate. Suitable materials for the substrate include, for example, insulating silicon, fused silicon dioxide, silicate glass, alumina, aluminosilicate ceramic, an epoxy, an epoxy composite such as glass fiber reinforced epoxy, polyester, polyimide, polyamide, or polycarbonate.

A variety of conductive materials can be used to form the working electrode 28. Suitable materials include, for example, carbon, conductive polymers, and metals. Examples of useful metals include gold, platinum, palladium, tantalum, tungsten, and their alloys, as well as metallic compounds like titanium nitride, and ruthenium dioxide. The preferred conductors do not corrode rapidly in aerated aqueous 0.1 M NaCl near neutral pH when a potential of 0.2 volts positive of the potential of the saturated calomel electrode (SCE) is applied. The corrosion current density is preferably less than $10^{-4}$ A cm$^{-2}$, and more preferably less than $10^{-7}$ A cm$^{-2}$.

Thin films of these materials can be formed by a variety of methods including, for example, sputtering, reactive sputtering, physical vapor deposition, plasma deposition, chemical vapor deposition, printing, and other coating methods. Discrete conductive elements may be deposited to form each of the working electrodes, for example, using a patterned mask. Alternatively, a continuous conductive film may be applied to the substrate and then the working electrodes can be patterned from the film using for example, known photolithographic techniques.

The working electrode can have a variety of shapes, including, for example, square, rectangular, circular, ovoid, and the like. The working electrode may have dimensions (e.g., length, width, or diameter) which can be of any size. In one embodiment the surface area may be 50 $\mu$m or less. In some embodiments, the working electrodes are three dimensional structures, and can have a surface area of $1 \times 10^{-4}$ cm$^2$ or less. Multiple electrodes may be used in an array.

When using film electrodes, the counter and reference electrodes may be substrate containing the working electrode. Alternatively, the counter and reference electrodes may be formed on the substrate containing the working electrode. They can be located on a surface that also comprises the working electrode or on a different surface. It is not necessary for each working electrode to have a dedicated counter electrode or reference electrode. The same counter or reference electrode can serve multiple, or even all, electrodes of an array. A single electrode, such as an Ag/AgCl electrode, can serve as both counter and reference electrode. Preferably the reference electrode is one that does not leach ions and maintains a constant potential. The reference electrode can be, for example, a silver wire or structure, in contact with the electrolytic solution. The surface of the silver wire or structure can be partially oxidized to produce AgCl chemically, or electrochemically.

The Redox Polymer

The electrode is coated with a thin film of a redox polymer. The redox polymer 40 is deposited on the electrode 28. When multiple working electrodes are used, the redox polymer 40 is not deposited on the substrate between the electrodes, thus maintaining the electrical isolation of the working electrodes from each other. Another specific method whereby a redox polymer can be deposited exclusively on the electrode is electrophoresis. This is a preferred method for coating electrodes of an array when their diameter is small, usually smaller than 50 $\mu$m.

Redox hydrogels are formed from the crosslinked redox polymers upon their immersion in aqueous solutions. The redox hydrogels provide for transport of electrons between the electrode and the detection marker. One type of redox polymer is a redox hydrogel which typically contains water in an amount of at least 10 wt % of the redox polymer. Water soluble molecules usually permeate through the redox hydrogel rapidly. Electron conduction in the redox hydrogel is believed to occur through electron exchange between polymer segments that, being tethered directly or indirectly to the electrode, do not leach out but are nevertheless mobile within a limited, small radius.

In general, the redox polymer includes electroreducible and electrooxidizable functions, termed redox centers. These have redox potentials that are a few hundred millivolts above or below the redox potential of the standard calomel electrode (SCE). Preferably, the redox centers of the potentials of the polymers are not more reducing than about −400 mV and not more oxidizing than about +800 mV versus SCE, and most preferably are not more reducing than about −150 mV and not more oxidizing than about +400 mV versus SCE at neutral pH. The most preferred redox polymers have osmium, ruthenium, or cobalt redox centers and a redox potential ranging from about −150 mV to about +400 mV versus SCE.

In general, redox polymers suitable for use in the invention have bonds or charges that prevent, or substantially reduce, the diffusional outflux or loss of the redox species during the period of time in which the sample is being analyzed. The bond between the redox species and the polymer may be covalent, coordinative, or ionic. Useful redox polymers and methods for producing them are described in U.S. Pat. Nos. 5,264,104; 5,356,786; 5,262,035; 5,320,725; and 5,665,222, incorporated herein by reference. Although many organic or organometallic redox centers can be incorporated in or bound to a polymer and used in the system of the present invention, the preferred redox species are transition metal complexes. The more preferred transition metal complexes are osmium, ruthenium, iron, and cobalt complexes. The most preferred are osmium and ruthenium complexes.

One type redox polymer contains a redox species covalently bound to a polymer. An example of such a polymer is poly(vinylferrocene). Another type of redox polymer contains an electrostatically bound redox species. Typically, this type of redox polymer comprises a charged polymer coupled to an oppositely charged redox species. Examples of this type of redox polymer include a negatively charged polymer such as Nafion® (DuPont) in which a positively charged redox species, containing one or more of osmium or ruthenium polypyridyl cations is distributed. Another example of such a polymer is a polymer comprising positively charged functions, such as quaternized poly(4-vinyl pyridine) or quaternized poly(1-vinyl imidazole), and negatively charged redox species such as ferricyanide and ferrocyanide. The redox polymer may consist of a highly charged redox species, that itself may be polymeric and have multiple redox centers, and an oppositely charged polymer, the redox polymer being bound electrostatically to the oppositely charged polymer.

In another embodiment of the invention, suitable redox polymers include a redox species coordinatively bound to a polymer. For example, the redox species may be formed by complexing of osmium, ruthenium or cobalt ions with 2,2'-bipyridine and also with poly(1-vinyl imidazole) or poly(4-vinyl pyridine) or with a copolymer of either of these.

The preferred redox species are complexes of transition metals, most preferably complexes of osmium, ruthenium, or cobalt. The complexes comprise one or more heterocyclic ligands, each ligand having two or more rings, each ring with one or more nitrogen atoms, such as 2,2'-bipyridine, 1,10-phenanthroline, 2,2',2"-terpyridine, or derivatives thereof. More preferred complexes include osmium cations complexed with two ligands, each ligand containing 2,2'-bipyridine, 1,10-phenanthroline, or derivatives thereof, the two ligands not necessarily being the same. In the preferred complexes of osmium, ruthenium, or cobalt, three or more of the coordination sites of the metal ion are nitrogen-occupied, and the number of ligands ranges from 1 to 3. In the most preferred complexes, five of the coordination sites are nitrogen-occupied, and the number of ligands ranges from 2 to 3.

The preferred redox species exchange electrons rapidly with each other, in a process known as self-exchange, and also with the working electrode, so that the complexes can be rapidly electrooxidized and electroreduced. While they can be electrostatically held in the redox polymer, the preferred redox species are coordinatively or covalently bound to the polymer. The preferred polymers of the type that bind the ions of the metal ion complex coordinatively, typically have nitrogen-containing heterocyclic rings, such as pyridine, imidazole, or derivatives thereof. These bind, as ligands, to the cations of the redox species.

Preferred polymers for complexation with redox species, such as the osmium complexes, described above, include polymers and copolymers of poly(1-vinyl imidazole) (referred to as "PVI"), poly(4-vinyl pyridine) (referred to as "PVP"), and pyridinium-modified poly(acrylic acid). Suitable copolymer substituents of poly(1-vinyl imidazole) include acrylonitrile, acrylamide, acrylhydrazide, and substituted or quaternized N-vinyl imidazole. The osmium complexes coordinatively bind with the imidazole and pyridine groups of the polymer. In copolymers comprising non-coordinating mers, or weakly coordinating ones, such as acrylamide or acrylonitrile, and also strongly coordinating mers such as N-vinyl-imidazole or 4-vinylpyridine, the ratio of osmium complexes to imidazole and/or pyridine groups ranges from 1:10 to 1:1, preferably from 1:2 to 1:1, and more preferably from 3:4 to 1:1. Also, the preferred ratio of the number of complexed transition metal atoms and polymerized vinyl functions ranges from about 1:2 to about 1:30, and more preferably from about 1:5 to about 1:20.

Examples of other redox species include quinones and species that in their oxidized state have quinoid structures, such as Nile blue and indophenol. The preferred quinones and quinoids do not have hydrogen atoms in their six-membered rings.

The first member binds to the redox polymer for example, by hydrazide functional groups. The redox polymer 40 may also include a binding agent 30 for binding the first ligand 32 of the amplified DNA 21. In a preferred embodiment the binding agent 30 is an antibody, a fragment of an antibody, avidin or streptavidin. The binding agent binds to the first ligand 32 of the amplified DNA 21 thereby immobilizing the amplified DNA 21 on the electrode 28. The binding agent 30 is preferably covalently bound to the redox polymer, for example by carbodiimide coupling of carboxylate functions of the antibody, avidin or streptavidin, to hydrazide functions of polymers like PAH of FIGS. 4A–4B.

In one embodiment, the polymer is a copolymer of PVI or PVP with polyacrylamide ("PAA") in which Os(bpy)$_2$ Cl$^{+/2+}$ is coupled to the imidazole or pyridine functions respectively. To form hydrazide functional groups in this redox polymer, for subsequent covalent attachment of the binding agent 30 and for crosslinking a portion of the amide functions is converted to hydrazide functions by reaction with hydrazine, according to known processes. Typically, at least 5% of the amide groups are converted, preferably, at least 10% of the groups are converted, and more preferably, at least 20% of the groups are converted. The ratio of hydrazide groups to unmodified amide groups of the resulting polymer is typically 1:1 to 1:20, and preferably 1:2 to 1:10. The ratio of PVI or PVP to PAA is typically 5:1 to 1:15, preferably, 2:1 to 1:12, and, more preferably, 1:1 to 1:10. The PAA copolymer in which some of the amides are converted to hydrazides is termed PAH.

In another embodiment, the polymer is a modified poly (acrylic acid). A portion of the carboxylic acid functions of the poly(acrylic acid) are converted to pyridine or imidazole carrying functions. These can be amides, such as those formed with 4-(aminoalkyl)-pyridine, particularly 4-(2-aminoethyl)-pyridine, that can be covalently attached through carbodiimide coupling. The pyridine and imidazole groups can then be used for coordinative binding with the osmium complexes. Typically, at least 2%, preferably, at least 5%, and, more preferably, at least 10%, of the carboxylic acid functions are converted to functions with pyridine or imidazole rings. At least a portion of the remaining carboxylic acid groups are converted to hydrazide groups to facilitate the crosslinking redox polymer and for covalent attachment of the binding agent or crosslinking. Typically, at least 2%, preferably, at least 5%, and, more preferably, at least 10%, of the residual carboxylic acid groups are converted to hydrazide groups.

A variety of methods may be used to immobilize a redox polymer on an electrode surface. One method is adsorptive immobilization. This method is particularly useful for redox polymers with relatively high molecular weights, for example, greater than about $10^4$ daltons, preferably greater than $10^5$ daltons, and most preferably greater than $10^6$ daltons. The molecular weight of a polymer may be increased, for example, by cross-linking with a di- or polyfunctional cross-linking agent, such as those listed in the Pierce catalog, 1994, pages T155–T167. Examples of functions of cross-linking agents useful in the invention include epoxy, aldehyde, N-hydroxysuccinimide, halogen, imidate, thiol, and quinone functions. Examples of crosslinkers include poly(ethylene glycol) diglycidyl ether and cyanuric chloride. Poly(ethylene glycol) diglycidyl ether (PEGDGE) having a molecular weight ranging from about 400 to 600 daltons is most preferred. Other crosslinking agents may also be used.

In another embodiment, the redox polymer is immobilized by covalent bonding to a functionalized electrode surface. Carbon surfaces can be modified for covalent attachment of a redox polymer, for example, by electroreduction of a diazonium salt or by oxidation with hydrogen peroxide in the presence of divalent iron ions at a pH of less than 6. As an illustration, reduction of a diazonium salt formed upon diazotization of p-aminobenzoic acid modifies a carbon surface with phenylcarboxylic acid groups. These groups can then be activated by a carbodiimide, such as 1-ethyl-3-(3-dimethylaminopropyl)-carbodiimide hydrochloride. The activated groups are then bound with a hydrazide or with an amine-functionalized redox couple, such as, for example, PAH, the polymer of FIG. 4A.

The redox hydrogel optionally also contains additional compounds that are useful in the verification of the amplification. In particular, it may contain a substrate generating enzyme. This enzyme may catalyze the generation of an electroreducible detection compound like hydrogen peroxide by catalyzing a reaction of stable and preferably nontoxic reagents. As a result of the internal generation of the detection compound, within the film on the electrode, the need for adding unstable or toxic agents to the analyzed fluid is obviated.

An example of a substrate generating enzyme that may be immobilized in the redox polymer is choline oxidase, which generates hydrogen peroxide in situ within the redox polymer film on the electrode. Hydrogen peroxide is catalytically electroreduced when the peroxidase detection marker of the third member is in contact with the redox hydrogel. In the absence of either the peroxidase detection marker or the redox polymer the film is not electrocatalytic for $H_2O_2$ reduction in the applied potential range between −0.1 V (SCE) and +0.4 V (SCE), the film is electrocatalytic through this range when both the peroxidase and the redox polymer are co-immobilized in it. The redox or reaction centers of choline oxidase do not rapidly exchange electrons with those of the redox hydrogel, so the presence of the enzyme in the hydrogel and the presence of choline do not change the signal, typically measured as current or a potential. Choline oxidase catalyzes the reaction of molecular oxygen with choline, whereby hydrogen peroxide and betaine aldehyde are formed.

The Catalyst

A variety of catalysts 38 can be used as part of the detection marker 36. Exemplary catalysts are enzymes that catalyze an electrochemical reaction of a detection compound or catalyze the conversion (e.g., hydrolysis) of a difficult to electrooxidize compound to one that can be electrooxidized at lower oxidizing potentials. A variety of enzymes are useful including, for example, peroxidases for use with hydrogen peroxide, glucose oxidase and glucose dehydrogenase for use with glucose, and lactate oxidase and lactate dehydrogenase for use with lactate, as well as alkaline and other phosphatases. Preferably, thermostable enzymes (enzymes capable of operation for at least 1 hour at 37° C. with less than 1% reduction in activity) are used. Soybean peroxidase is one example of a thermostable enzyme.

The catalyst may also be an enzyme accelerating the conversion (e.g., hydrolysis) of a precursor compound to a more easily electrooxidizable or electroreducible compound. An example of such a catalyst is alkaline phosphatase, an enzyme accelerating the hydrolysis of the phosphate ester of p-aminophenol to readily electrooxidizable p-aminophenol.

The Detection Compound

The detection compound is usually a compound (e.g., a substrate) that is electroreduced or electrooxidized in the presence of the labeling catalyst or enzyme. It can also be a compound that is easily electrooxidized or is easily electroreduced and is formed for example in an enzyme-catalyzed hydrolysis reaction from an electrochemically less active precursor.

EXAMPLES

The invention may be better understood by reference to the following examples, which are not intended to limit the scope of the invention.

Amplification of an 800 base template was verified in a 10 minute test on a 2 $\mu$L sample of the PCR product solution. For verification, digoxigeninylated primers and d-UTP-16-biotin were added to the amplification solution. The resulting amplified product was digoxigenin-labeled at its 3'-end and was also labeled with multiple biotin functions along its chain.

The detecting electrode was coated with an electron-conducting redox hydrogel to which anti-digoxin monoclonal antibody was covalently bound. The amplified DNA was captured by the electrode through conjugation of its 3'-digoxigenin with the antibody. Exposure to a solution of horseradish peroxidase labeled avidin (Av-HRP) led to capture of the enzyme, and switched the redox hydrogel from a non-catalyst to a catalyst for $H_2O_2$ electroreduction. The switching resulted in an $H_2O_2$ electroreduction current density of 2.1±0.9 $\mu$A cm$^{-2}$ in $10^{-4}$ M $H_2O_2$ at Ag/AgCl potential and at 25° C.

The separationless method of the invention required only a miniature low-power potentiostat, which was of the size of a matchbox and was made of inexpensive components. The verification was completed in 10 minutes the required time being determined by the mass-transport conditions. The test utilized 30 $\mu$L of the product solution per cm$^2$ of electrode, amounting to 2 $\mu$L in case of the 3 mm diameter electrodes actually used. The scheme of the verification process is shown in FIGS. 3A–3B.

Figures 4A, 4B:
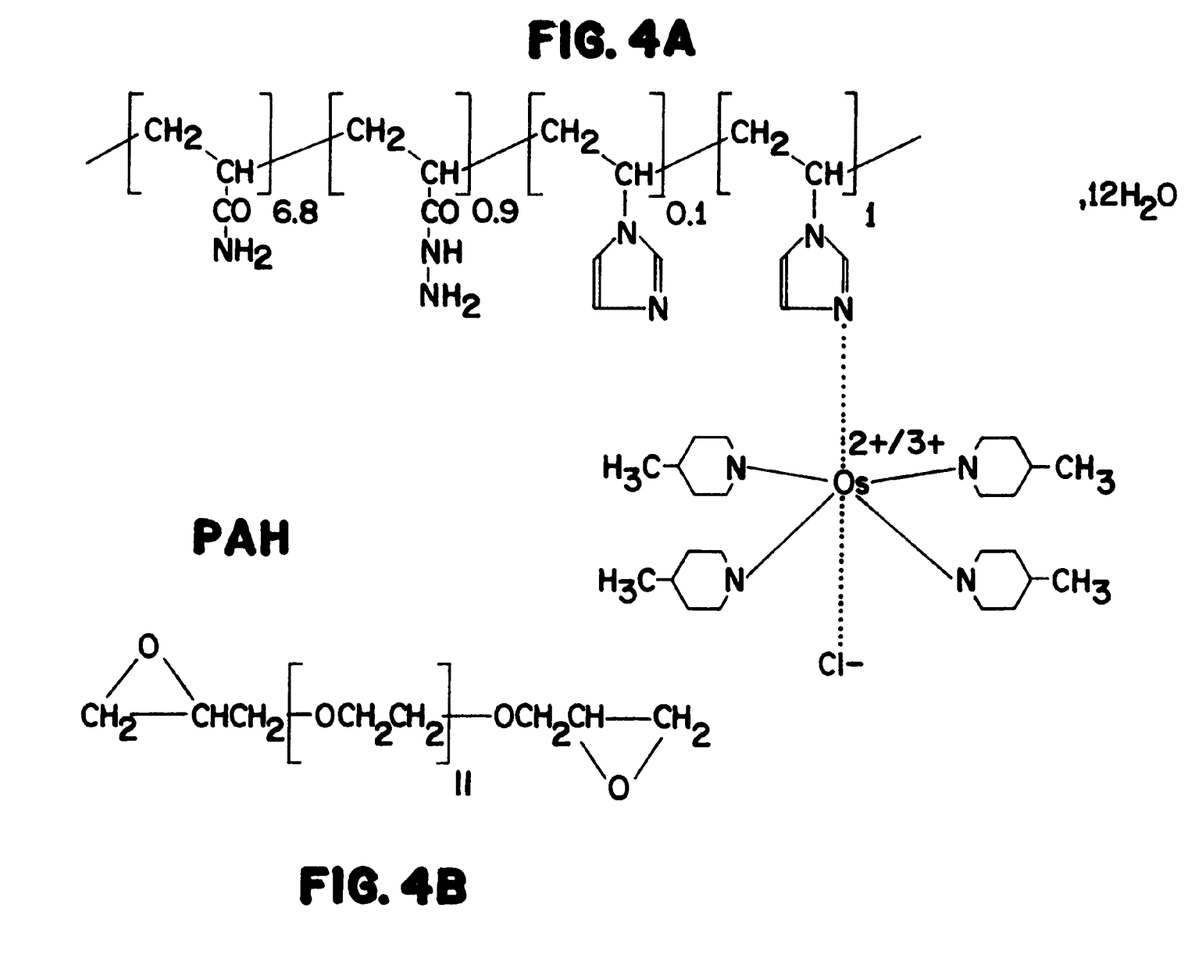
FIG. 4A is a diagram showing the structure of the water soluble copolymer of acrylamide and vinylimidazole, modified with hydrazine and $[Os(dmebpy)_2Cl]^{+/2+}$, termed PAH (dmebpy=4,4'-dimethyl-2,2'-bipyridine).
FIG. 4B shows the structure of the cross-linking agent, PEGDGE.

Reagents. Sodium periodate (cat# 31,144-8) and Tween 20 (cat# 27,434-8) were purchased from Aldrich. Av-HRP (cat# A-3151), biotin (cat# B 4501) and monoclonal anti-digoxin (cat# D8156) (mouse IgG1 isotype) in ascites fluid were purchased from Sigma. Poly(ethylene glycol 400 diglycidyl ether) (PEGDGE), technical grade, was purchased from Polysciences (cat# 08211). The redox polymer based on a 7:1 copolymer of acrylamide and 1-vinylimidazole partially complexed with [Os(dmebpy)$_2$Cl]$^{+/2+}$ dmebpy=4, 4'-dimethyl-2,2'-bipyridine with part of the amide functional groups converted to hydrazide functional groups (PAH) was synthesized as previously described by de Lumley-Woodyear, et al., *Anal. Chem.* 1995, 67, 1332. Its structure is shown in FIG. 4A. FIG. 4B shows the structure of the cross-linker, PEGDGE.

Electrodes and Electrochemical Equipment. Rotating disk electrodes were prepared by embedding a vitreous carbon rod (3 mm diameter, V10 Atomergic) in a Teflon™ shroud using a low viscosity epoxy resin (Polyscience, catalog No 01916). Electrochemical measurements were performed with a Bioanalytical Systems CV-1B potentiostat. The signal was recorded on a Bioanalytical Systems XYT recorder. Rotating disk electrode experiments were performed with a Pine Instruments AFMSRX rotator with an MSRX speed controller. The electrochemical measurements were performed using a 14 mM phosphate pH 7.4 buffer in a three-electrode cell with a rotating (1000 rpm) glassy carbon working electrode, an Ag/AgCl Bioanalytical Systems reference electrode, and a platinum wire as counter electrode.

Films: Films were formed on the 3 mm glassy carbon electrodes by crosslinking of hydrazide functions of the redox polymer (PAH) with epoxide functions of PEGDGE. 5 mg mL$^{-1}$ PAH and 0.21 mg mL$^{-1}$ PEGDGE were mixed in a 2:1 ratio. 3 $\mu$L of the 2:1 solution was spread on the electrode, then allowed to dry and to cure at room temperature for 24 hours. The films were uniform, shiny, swelled in water to electron conducting hydrogels and adhered well to vitreous carbon. The antidigoxin IgG solution (0.1 mL; concentration 6.7 mg mL$^{-1}$) was purified using a HiTrap protein G affinity column from Pharmacia Biotech by elution with 0.1 M glycine, then by dialysis against pH 7.4 phosphate buffer solution (0.15 M NaCl, 0.020 M sodium phosphate), using Amicon Centriprep 30 tubes (4×30 minutes at 2700 g). Next, carbohydrate groups on the antibody $C_H2$ domain were oxidized to formyl groups by mixing 1 mL of the dialyzed antibody solution with 1 mL of sodium meta-periodate (10 mg mL$^{-1}$). After oxidation of the antibody oligosaccharides, the excess sodium periodate was removed by dialysis using an Amicon Centriprep 30 tube.

The concentration of the resulting antidigoxin solution was 0.2 mg mL$^{-1}$ as measured with a biuret kit, using BSA as the standard. An 8 μL drop of this mixture was deposited on the redox polymer modified electrode. The electrode was kept for 16 hours in a 25° C. chamber, the atmosphere of which was saturated with water. The intact antibody molecules were immobilized by forming hydrazones between aldehydes of the monoclonal antidigoxin and hydrazide functions of the polymer. The electrode was then rotated at 1000 rpm for 20 minutes in a 2% solution of PEGDGE in phosphate buffer. Next the electrode was reacted for 20 minutes in pH 4.6 acetate buffer with 2% glutamate to eliminate all residual unreacted epoxide functions. The electrode was then incubated with 0.2% BSA for 10 minutes and stored in phosphate buffer solution at 4° C.

PCR: An 800 base pair DNA fragment was amplified in a standard PCR amplification solution, to which the 3'-digoxigeninylated-primer and dUTP-16-biotin were added. With these the PCR amplified product was terminally labeled with digoxigenin and was also labeled with multiple biotin functions along the chain. The PCR was performed on 1 μL of the template solution, plasmid pTX152 encoding a scFvdig antibody gene. The template solution was mixed with 99 μL of amplification master mix (89 μL water, 10 μL of amplification buffer from Boehringer, 1 μM (each) BamH1 biotinylated primer (5' biotin CTTCTTGATGGATCCGTCCTCGGGGTCTT) [SEQ. ID NO: 1] and #4 digoxigeninylated primer from Genosys (5' digoxigenin-TGGACCAACAACATCGGT) [SEQ. ID NO: 2], 200 μM dATP, dCTP, dGTP (each), 144 μM dTTP, 40 μM dUTP-16-biotin, 5 U of Taq DNA polymerase from Boehringer (cat# 1146165)). Amplification was performed in a thermocycler by using the following program: 1 cycle at 94° C. for 2 minutes, 53° C. for 2 minutes, 72° C. for 3 minutes, followed by 28 cycles at 94° C. for 1 minutes, 53° C. for 2 minutes, 72° C. for 3 minutes and 1 cycle at 72° C. for 7 minutes. At the end of the program the tubes were held at 4° C. The resulting double stranded DNA consisted of 800 base pairs, some of which were modified with biotin, and located at the end of a 16 carbon spacer arm. In addition, one end of the strand was labeled with digoxigenin.

Verification Procedure. It was found that both the DNA and the Av-HRP conjugation reactions with the film on the electrode were mass transport (reactant concentration and angular velocity) controlled. In the verification procedure 2 μL of the PCR sample were mixed with 700 μL of 0.1 M acetate buffer containing 0.1 M NaCl and 0.2% Tween 20. The amplified DNA was captured by the redox hydrogel on the electrodes through conjugation of digoxigenin functions with antidigoxin antibodies, by rotating the electrodes at 1000 rpm in the diluted PCR solution for 5 minutes. Following capture of the amplified DNA 700 μL of 1 μg mL$^{-1}$ Av-HRP were added and the electrode was rotated for an additional 5 minutes, so as to bind to the electrode via the captured DNA the Av-peroxidase.

Figure 5:
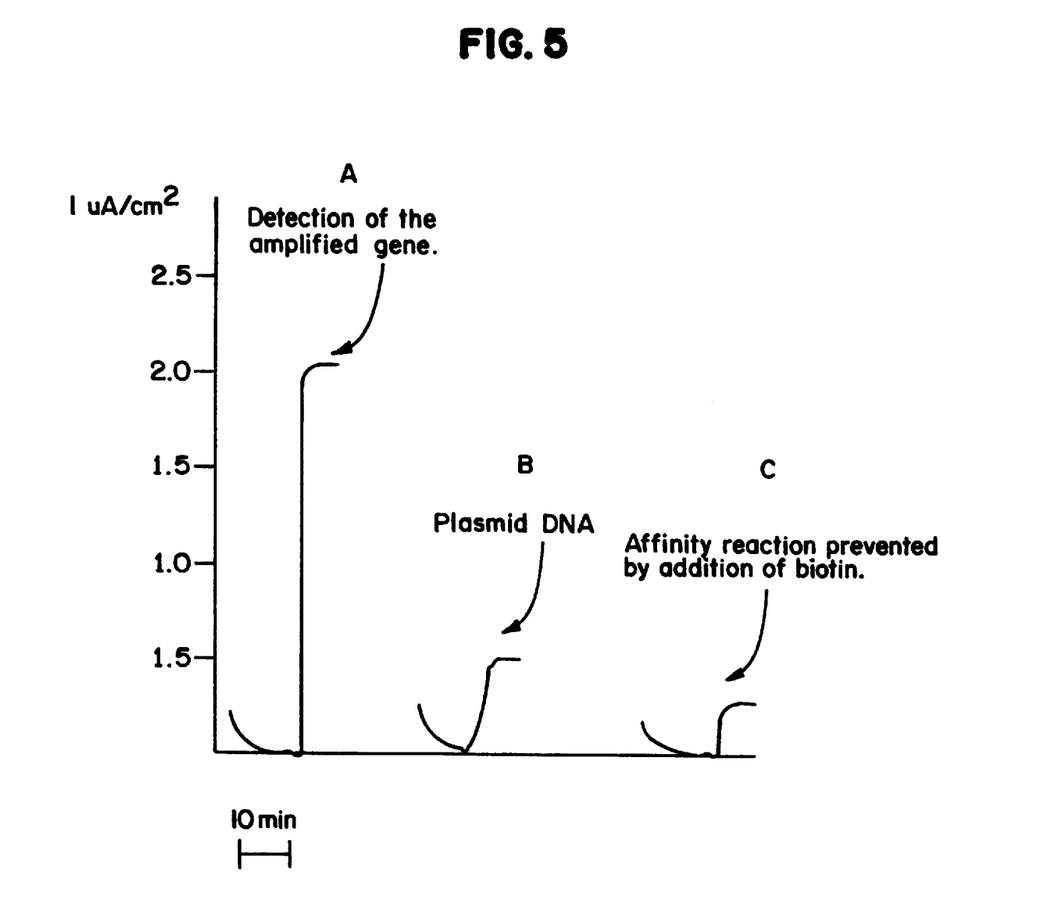
FIG. 5 is a graph showing the increase in the electroreduction current upon raising the concentration of hydrogen peroxide from zero to $10^{-4}$ M in the presence of: (A) avidinylated HRP and post-PCR sample; (B) avidinylated HRP and pre-PCR sample; and (C) biotin-blocked avidinylated HRP and post-PCR sample.

When the completed electrode was immersed in 25° C. pH 7.4 phosphate buffer the current density rose to 2.1±0.9 μA cm$^{-2}$ at 0.0 V versus Ag/AgCl upon adding H$_2$O$_2$ to 10$^{-4}$M concentration (FIG. 5). In an identical experiment, but with the binding sites of Av-HRP blocked with excess of biotin, so as to prevent specific binding of Av-HRP to the captured amplification product on the electrode, the current density rose only to 0.3±0.2 μA cm$^{-2}$. When the electrode was prepared with 2 μL of the amplification mixture (plasmid DNA, nucleotides, biotinylated oligonucleotides, biotinylated and digoxigeninylated primers), but without executing the temperature cycles necessary for actual amplification the current density was 0.5±0.2 μA cm$^{-2}$ (Table 1).

As is evident from Table 1 and from FIG. 5, the simple and straightforward amperometric test rapidly detected the PCR product. FIG. 5 shows the increase in the electroreduction current upon raising the H$_2$O$_2$ from zero to 10$^{-4}$ M. The coated electrode was incubated with 700 μL of 0.1 M acetate buffer containing 0.1 M NaCl and 0.2% Tween 20 mixed with the following: (A) 0.7 μg mL$^{-1}$ avidinylated HRP and 2 μL of the PCR sample; (B) 0.7 μg mL$^{-1}$ avidinylated HRP and 2 μL of the plasmid DNA solution with nucleotides, biotinylated oligonucleotides, biotinylated and digoxinylated primers, each at a concentration identical with its concentration in (A) before the PCR; (C) 0.7 μg mL$^{-1}$ avidinylated HRP the binding sites of which were blocked with biotin and 2 μL of the PCR sample.

Because the time required for completion of the verification was controlled by mass transport of the macromolecular reactants DNA and Av-HRP to the surface of the electrode, it is projected that, in a flow channel where the greater than 100-fold dilution of the PCR product caused by the need for a large volume now required for a rotating electrode is obviated, and where the undiluted PCR product solution and a more concentrated Av-HRP solution are used, the test times will be much shorter than 10 minutes, and will usually be less than one minute. Because 30 μL of the PCR solution were required per cm$^2$, the volume of PCR solution to be used with a 10 μm diameter microelectrode is projected at 0.02 nL. Extrapolation of the observed current density of 2.1 μA/cm$^2$ and correction for the change from semi-infinite planar electron diffusion in the macroelectrode to radial electron diffusion in a similar H$_2$O$_2$ electroreducing 10 μm diameter microelectrode (Horrocks, et al., *Anal. Chem.* 1993, 65, 3605; Sakai, et al., *J. Phys. Chem.* 1995, 99, 11896) indicates a projected current of 4 nA, which is easily measurable with a simple and inexpensive low power potentiostat.

TABLE 1

H$_2$O$_2$ Electroreduction Current Densities ± PCR Product

| PCR product | A-HRP | biotin | plasmid DNA, components of PCR mix. | Signal μA cm$^{-2}$ |
|---|---|---|---|---|
| + | + | − | − | 2.1 |
| + | + | + | − | 0.5 |
| − | + | − | + | 0.3 |

We claim:

1. A method for verifying amplification of a nucleic acid molecule in a sample, comprising:
   synthesizing, in an amplification process, a nucleic acid molecule labeled with a first ligand and with a second ligand;
   immobilizing the nucleic acid molecule on an electrode by binding the first ligand to a redox polymer film disposed on the electrode;
   binding a detection marker comprising a catalyst to the second ligand; and
   correlating a change in current or potential at the electrode with a change in the rate of an electrochemical reaction catalyzed by the detection marker catalyst and with amplification of the nucleic acid molecule,
   wherein the correlating step is accomplished without separating immobilized nucleic acid molecules from the sample.

2. The method of claim 1 where said correlating a change comprises measuring an electrical current.

3. The method of claim 1 where said correlating a change comprises measuring an electrical potential.

4. The method of claim 1, where the catalyst is an enzyme.

5. The method of claim 4 where the enzyme is an oxidoreductase.

6. The method of claim 5 where a substrate of the oxidoreductase is oxidized by the electrooxidized redox polymer or electroreduced by the electroreduced redox polymer.

7. The method of claim 6 where the oxidoreductase is a peroxidase and the substrate is hydrogen peroxide.

8. The method of claim 6 where the oxidoreductase is an oxidase.

9. The method of claim 4 where the enzyme catalyzes the hydrolysis of a substrate to a product, the product being electrooxidized at a less oxidizing potential than the substrate.

10. The method of claim 1, wherein said catalyst comprises a peroxidase.

11. The method of claim 10, wherein said peroxidase is thermostable.

12. The method of claim 11, wherein the thermostable peroxidase is soybean peroxidase.

13. The method of claim 1, wherein said redox polymer comprises a binding agent covalently bound thereto, and wherein binding of the first ligand to the redox polymer comprises binding the first ligand to the binding agent.

14. The method of claim 13, wherein said binding agent comprises avidin, streptavidin, an antibody or an antibody fragment.

15. The method of claim 1, wherein said detection marker further comprises avidin, streptavidin, an antibody or a fragment of an antibody.

16. The method of claim 1, wherein the redox polymer film is hydrated.

17. The method of claim 16, wherein the weight of water in the hydrated redox polymer is more than 10% of the weight of the redox polymer.

18. The method of claim 1, wherein the amplification process is carried out with a mixture comprising a ligand labeled primer.

19. The method of claim 18, wherein the amplification process is carried out with a first primer labeled with a first ligand and with a second primer labeled with a second ligand, the first primer differing from the second primer and the first ligand differing from the second ligand.

20. The method of claim 19, wherein the second ligand comprises a biotin function.

21. The method of claim 19, wherein the first ligand or the second ligand comprises a biotin function.

22. The method of claim 13, wherein said first ligand comprises digoxigenin and said binding agent comprises an anti-digoxin antibody.

23. The method of claim 1, wherein said second ligand comprises biotin, and wherein said detection marker comprises a biotin function.

24. The method of claim 22, wherein said detection marker comprises peroxidase.

* * * * *

UNITED STATES PATENT AND TRADEMARK OFFICE
CERTIFICATE OF CORRECTION

PATENT NO. : 6,638,716 B2
APPLICATION NO. : 09/145776
DATED : October 28, 2003
INVENTOR(S) : Adam Heller et al.

Page 1 of 1

It is certified that error appears in the above-identified patent and that said Letters Patent is hereby corrected as shown below:

In the Specification

In column 1, line 5, please add the following paragraph above the FIELD OF THE INVENTION section:

--STATEMENT REGARDING FEDERALLY SPONSORED RESEARCH
This invention was made with government support under Grant no. N00014-02-1-0144 awarded by the Office of Naval Research; and 9505956 awarded by the National Science Foundation. The government has certain rights in the invention.--

Signed and Sealed this
Twenty-ninth Day of September, 2015

Michelle K. Lee
*Director of the United States Patent and Trademark Office*